(12) United States Patent
Tonelli et al.

(10) Patent No.: US 10,377,857 B2
(45) Date of Patent: Aug. 13, 2019

(54) POLYAMIDES MODIFIED WITH (PER)FLUOROPOLYETHER SEGMENTS

(71) Applicant: SOLVAY SPECIALTY POLYMERS ITALY S.P.A., Bollate (IT)

(72) Inventors: Claudio Adolfo Pietro Tonelli, Paderno D'adda (IT); Ivan Wlassics, Garessio (IT); Giuseppe Marchionni, Milan (IT); Sanjay Gurbasappa Charati, Gujarat (IN); Ritu Ahuja, Gujarat (IN); Gourav Upadhyay, Vadodara (IN)

(73) Assignee: SOLVAY SPECIALTY POLYMERS ITALY S.P.A., Bollate (Milan) (IT)

( * ) Notice: Subject to any disclaimer, the term of this patent is extended or adjusted under 35 U.S.C. 154(b) by 226 days.

(21) Appl. No.: 15/108,101

(22) PCT Filed: Dec. 19, 2014

(86) PCT No.: PCT/EP2014/078647
§ 371 (c)(1),
(2) Date: Jun. 24, 2016

(87) PCT Pub. No.: WO2015/097076
PCT Pub. Date: Jul. 2, 2015

(65) Prior Publication Data
US 2016/0326318 A1 Nov. 10, 2016

(30) Foreign Application Priority Data

Dec. 24, 2013 (IN) .......................... 3762/DEL/2013
Mar. 5, 2014 (EP) .................................. 14157760
Aug. 20, 2014 (EP) .................................. 14181627

(51) Int. Cl.
| | |
|---|---|
| *C08G 69/40* | (2006.01) |
| *C08G 69/42* | (2006.01) |
| *C07D 209/50* | (2006.01) |
| *C08G 65/00* | (2006.01) |
| *C08J 5/00* | (2006.01) |
| *C08J 5/04* | (2006.01) |
| *C08K 7/14* | (2006.01) |
| *C08G 65/332* | (2006.01) |
| *C08G 65/333* | (2006.01) |

(52) U.S. Cl.
CPC ........... *C08G 69/42* (2013.01); *C07D 209/50* (2013.01); *C08G 65/007* (2013.01); *C08G 65/3326* (2013.01); *C08G 65/33303* (2013.01); *C08G 65/33306* (2013.01); *C08G 65/33337* (2013.01); *C08G 69/40* (2013.01); *C08J 5/00* (2013.01); *C08J 5/043* (2013.01); *C08K 7/14* (2013.01); *C08G 2120/00* (2013.01); *C08G 2650/48* (2013.01); *C08J 2377/06* (2013.01)

(58) Field of Classification Search
CPC ...................................................... C08G 69/40
USPC ......................................................... 528/310
See application file for complete search history.

(56) References Cited

U.S. PATENT DOCUMENTS

| | | |
|---|---|---|
| 3,665,041 A | 5/1972 | Sianesi et al. |
| 3,715,378 A | 2/1973 | Sianesi et al. |
| 3,810,874 A | 5/1974 | Mitsch et al. |
| 3,847,978 A | 11/1974 | Sianesi et al. |
| 3,876,617 A | 4/1975 | Caporiccio et al. |
| 4,278,776 A * | 7/1981 | Mauro .................... C08L 27/16 525/178 |
| 5,109,103 A | 4/1992 | Re et al. |
| 5,371,272 A | 12/1994 | Marchionni et al. |
| 5,476,910 A | 12/1995 | Turri et al. |
| 5,508,380 A | 4/1996 | Turri et al. |
| 5,686,522 A | 11/1997 | Tonelli et al. |
| 6,127,498 A | 10/2000 | Tonelli et al. |

FOREIGN PATENT DOCUMENTS

| | | |
|---|---|---|
| EP | 1864685 A1 | 12/2007 |
| WO | 2009010533 A1 | 1/2009 |
| WO | 2010049365 A2 | 5/2010 |
| WO | 2011082046 A1 | 7/2011 |
| WO | 2011082063 A1 | 7/2011 |

* cited by examiner

*Primary Examiner* — Duc Truong

(57) ABSTRACT

The present invention relates to thermoplastic polyamides (PA) comprising recurring units derived from a PFPE dicarboxylic acid (PFPA-DA) or a PFPE diamine (PFPE-NN) in a defined weight amount with respect to other units derived from the other monomers used in the course of polymerization. Polyamides (PA) are endowed with improved surface properties, chemical resistance and reduced brittleness and do not require the addiction of impact modifiers.

20 Claims, No Drawings

POLYAMIDES MODIFIED WITH (PER)FLUOROPOLYETHER SEGMENTS

CROSS-REFERENCE TO RELATED APPLICATIONS

This application is a U.S. national stage entry under 35 U.S.C. § 371 of International Application No. PCT/EP2014/078647 filed Dec. 19, 2014, which claims priority from Indian provisional application No. 3762/DEL/2013, filed on Dec. 24, 2013, European patent application No. 14157760.1, filed on Mar. 5, 2014 and European patent application No. 14181627.2, filed on Aug. 20, 2014. The entire contents of these applications are explicitly incorporated herein by this reference.

TECHNICAL FIELD

The present invention relates to polyamides, in particular to thermoplastic polyamides, to methods for their synthesis and to the use of such polyamides in the manufacture of thermoplastic articles.

BACKGROUND ART

Thermoplastic polyamides are widespreadly used as engineering plastics, mainly in the manufacture of automotive and electronic components and in the field of packaging. For these applications, it is often required that the polyamides have high hydro- and oleo-phobilcity and that they also show low brittleness, i.e. low tendency to crack, especially when the polyamides are exposed to cold temperatures or mechanical stress. In order to reduce brittleness, either additives, in particular plasticizers (or impact modifiers), can be blended with the finished polyamide or polymerization can be carried out in the presence of comonomers that are able to reduce the Tg of the polyamide. However, the insertion of additives or the use of certain comonomers may alter or reduce other properties which would instead be desirable to retain or even increase, including hydro- and oleo-phobicity. Thus, it is generally difficult to improve all aforementioned properties by blending with additives or insertion of comonomers. There is therefore the need to provide thermoplastic polyamides showing increased chemical resistance and surface properties in combination with reduced brittleness, said polyamides not requiring being blended with additives, in particular plasticizers.

It is known that (per)fluoropolyethers (herein after "PFPEs") can be used as additives for other polymers in order to modify certain physical/chemical properties of the polymer concerned. It has been observed that, when PFPEs are physically blended to other polymers, they tend to segregate and to migrate to the surface during polymer processing; in some instances, the separation of the PFPE from the composition might reduce the durability of the composition and of the finished article obtained therefrom. Moreover and more important, in several applications (e.g. biomedical applications), the risk of separation of chemical components from compositions represents a toxicological concern, so the use of additives is not acceptable.

PFPEs can also be used as co-macromers in the course of polymerization, thereby obtaining modified polymers having a PFPE covalently bound thereto. For example, patent documents EP 1864685 A (SOLVAY SOLEXIS S.P.A.), U.S. Pat. No. 5,476,910 (AUSIMONT S.P.A.), U.S. Pat. No. 5,686,522 (AUSIMONT S.P.A.) and U.S. Pat. No. 5,109,103 (AUSIMONT S.P.A.) disclose polyurethanes (PUs), polyurethane/polyesters (PUs/PEs) or polyesters (PEs) that are modified with PFPEs.

Patent documents U.S. Pat. No. 6,127,498 (AUSIMONT S.P.A.), WO 2009/010533 (SOLVAY SOLEXIS S.P.A.) and U.S. Pat. No. 5,508,380 (AUSIMONT S.P.A.) relate to other polymers or polymer additives modified with PFPE segments or blocks; modified polymers containing PFPE segments or blocks and amido moieties are generically mentioned.

U.S. Pat. No. 3,876,617 (MONTEDISON S.P.A.) discloses elastomeric polyamides and copolyamides which can be obtained by reacting a PFPE diacid, preferably in the form of a reactive derivative, with a diamine. In particular, in U.S. Pat. No. 3,876,617 it is stated that the polyamides can also contain further monomeric units with more than two functions, like polycarboxylic acids, to an extent up to 30% in number with respect to the bifunctional units. The amount of PFPE diacid contained in these polyamides is high and, for this reason, the resulting polyamide is endowed with elastomeric properties. Furthermore, this document does not specifically disclose polyamides obtained by reaction of a PFPE diacid, a diamine and a polycarboxylic acid.

WO 2010/049365 (SOLVAY SOLEXIS S.P.A.) relates to polymers comprising PFPE segments as additives for hydrogenated polymers to give them good surface properties, in particular a low coefficient of friction (page 1, lines 1-3). This document discloses, inter alia, polyamide additives which can be obtained by reacting a non-fluorinated diamine with a PFPE having ester or carboxyl functionality, in an amount in equivalent of amino groups equal to that of the functional groups of the diamine (see page 10, lines 5 to 8).

WO 2011/082063 A (3M INNOVATIVE PROPERTIES COMPANY [US]) discloses copolymers comprising at least one PFPE segment, at least one polydiorganosiloxane segment and multiple aminooxyalkylamino groups of formula (XI):

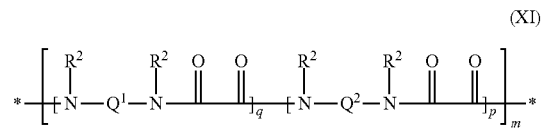

wherein:
Q¹ contains a PFPE segment;
Q² contains a polydiorganosiloxane segment;
each R² is independently hydrogen, alkyl, aralkyl or aryl,
each variable q, p and m is independently an integer to at least 1 and
each asterisk denotes a site of attachment to another group in the copolymer.

WO 2011/082046 A (3M INNOVATIVE PROPERTIES COMPANY [US]) discloses copolymers of formula (IV)

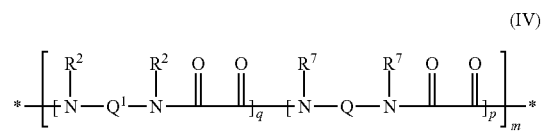

wherein:
each group Q¹ contains a perfluoropolyether segment;
each group Q is (a) an alkylene, (b) fluorinated alkylene, (c) heteroalkylene, (d) arylene, (e) a carbonylamino group linking a first group to a second group, wherein the first group and the second group are each independently an alkylene, fluorinated alkylene, heteroalkylene, arylene, a combination thereof, (f) part of a heterocyclic group that includes $R^7$ and a nitrogen to which $R^7$ is attached, or (g) a combination thereof;

each $R^2$ is independently hydrogen, alkyl, aralkyl, or aryl;

each $R^7$ is independently hydrogen, alkyl, aralkyl, aryl, or part of a heterocyclic group that includes Q and a nitrogen to which $R^7$ is attached;

each variable q, p, and m is an integer equal to at least 1;

each asterisk denotes a site of attachment to another group in the copolymer.

SUMMARY OF INVENTION

It has now been found that improved thermoplastic polyamides can be obtained by using a (per)fluoropolyether diamine (PFPE-NN) or a (per)fluoropolyether dicarboxylic acid (PFPE-DA) as co-monomers in the course of polymerization, in an amount of from 0.5 to 10% by weight, preferably in an amount of from 1% to 5% by weight with respect to the weight of the other monomers used in polymerization process. The thermoplastic polyamides of the invention show improved surface properties, in particular hydro- and oleo-phobicity with respect to non-modified polyamides and, at the same time, are endowed with improved chemical resistance and reduced brittleness, thereby avoiding or reducing the need for impact modifiers.

Accordingly, the present invention relates to a polyamide [polyamide (PA)] comprising, preferably consisting of, recurring units derived from monomers (A) and (B), wherein monomer (A) is selected from at least one of:

(i) a mixture of:
  one or more hydrogenated aliphatic, cycloaliphatic or aromatic diamine(s) [amine (NN)] or derivative(s) thereof; and
  one or more hydrogenated aliphatic, cycloaliphatic or aromatic dicarboxylic acid(s) [acid (DA)] or derivative(s) thereof;

(ii) one or more aminoacid(s) [aminoacid (AN)] or lactam(s) [lactam (L)] and wherein monomer (B) is at least one (per)fluoropolyether monomer (PFPE-M) selected from a PFPE-diamine (PFPE-NN) and PFPE-dicarboxylic acid (PFPE-DA), characterised in that the amount of monomer (B) ranges from 0.1 to 10% wt, preferably from 1 to 5% wt, with respect to the overall weight of monomers (A) and (B).

For the sake of clarity, the expression "recurring units derived from monomers (A) and (B)" identifies recurring units linked together through amido bonds between monomers (A) and (B).

According to a preferred embodiment of the invention, monomers (A) are a mixture of:
  one or more hydrogenated aliphatic, cycloaliphatic or aromatic diamine(s) [amine (NN)] or derivative(s) thereof; and
  one or more hydrogenated aliphatic, cycloaliphatic or aromatic dicarboxylic acid(s) [acid (DA)] or derivative thereof.

Polyamide (PA) can be obtained by means of a process (or method) which comprises co-polymerizing monomers (A) and (B) as defined above, said process comprising using an amount of monomer (B) ranging from 0.1 to 10% wt, preferably from 1 to 5% wt, with respect to the overall weight of monomers (A) and (B).

According to a preferred embodiment of the invention, polyamide (PA) is obtained by means of a process (or method) which comprises co-polymerizing a mixture of:

one or more hydrogenated aliphatic, cycloaliphatic or aromatic diamine(s) [amine (NN)] or derivative(s) thereof; and one or more hydrogenated aliphatic, cycloaliphatic or aromatic dicarboxylic acid(s) [acid (DA)] or derivative thereof;

and at least one monomer (B) as defined above said process comprising using an amount of monomer (B) ranging from 0.1 to 10% wt, preferably from 1 to 5% wt, with respect to the overall weight of amine (NN), acid (DA) and monomer (B).

Acid (DA) derivatives and (PFPE-DA) derivatives include notably salts, anhydrides, esters and acid halides, able to form amide groups; similarly, amine (NN) and (PFPE-NN) derivatives include notably salts thereof, equally able to form amide groups. Aminoacids (AN) derivatives include notably, salts, esters and acid halides, able to form amide groups.

Amine (NN) is generally selected from the group consisting of aliphatic alkylene-diamines, cycloaliphatic diamines, aromatic diamines and mixtures thereof. Said aliphatic alkylene-diamines are typically aliphatic alkylene diamines having 2 to 36 carbon atoms. Said aliphatic alkylene diamine is advantageously selected from the group consisting of 1,2-diaminoethane, 1,2-diaminopropane, propylene-1,3-diamine, 1,3-diaminobutane, 1,4-diaminobutane, 1,5-diaminopentane, 1,5-diamino-2-methyl-pentane, 1,4-diamino-1,1-dimethylbutane, 1,4-diamino-1-ethylbutane, 1,4-diamino-1,2-dimethylbutane, 1,4-diamino-1,3-dimethylbutane, 1,4-diamino-1,4-dimethylbutane, 1,4-diamino-2,3-dimethylbutane, 1,2-diamino-1-butylethane, 1,6-diaminohexane, 1,7-diaminoheptane, 1,8-diamino-octane, 1,6-diamino-2,5-dimethylhexane, 1,6-diamino-2,4-dimethylhexane, 1,6-diamino-3,3-dimethylhexane, 1,6-diamino-2,2-dimethylhexane, 1,9-diaminononane, 1,8-diamino-2-methyloctane, 1,6-diamino-2,2,4-trimethylhexane, 1,6-diamino-2,4,4-trimethylhexane, 1,7-diamino-2,3-dimethylheptane, 1,7-diamino-2,4-dimethylheptane, 1,7-diamino-2,5-dimethylheptane, 1,7-diamino-2,2-dimethylheptane, 1,10-diaminodecane, 1,8-diamino-1,3-dimethyloctane, 1,8-diamino-1,4-dimethyloctane, 1,8-diamino-2,4-dimethyloctane, 1,8-diamino-3,4-dimethyloctane, 1,8-diamino-4,5-dimethyloctane, 1,8-diamino-2,2-dimethyloctane, 1,8-diamino-3,3-dimethyloctane, 1,8-diamino-4,4-dimethyloctane, 1,6-diamino-2,4-diethylhexane, 1,9-diamino-5-methylnonane, 1,11-diaminoundecane, 1,12-diaminododecane, and 1,13-diaminotridecane. The aliphatic alkylene diamine preferably comprises at least one diamine selected from the group consisting of 1,6-diaminohexane, 1,8-diamino-octane, 1,10-diaminodecane, 1,12-diaminododecane and mixtures thereof. More preferably, the aliphatic alkylene diamine comprises at least one diamine selected from the group consisting of 1,2-diaminoethane, 1,4-diamino butane, 1,6-diaminohexane, 1,10-diaminodecane and mixtures thereof. Even more preferably, the aliphatic alkylene diamine is selected from 1,2-diaminoethane, 1,6-diaminohexane, 1,10-diaminodecane and mixtures thereof.

The aromatic diamine is preferably selected from the group consisting of meta-xylylene diamine (MXDA), and para-xylylene diamine. More preferably, the aromatic diamine is meta-xylylene diamine.

Diacid (DA) can be an aromatic dicarboxylic acid comprising two reactive carboxylic acid groups [acid (AR)] or an aliphatic dicarboxylic acid comprising two reactive carboxylic acid groups [acid (AL)]. For the purpose of the present invention, a dicarboxylic acid is considered as "aromatic" when it comprises one or more than one aromatic group. Non limitative examples of acids (AR) are notably phthalic acids, including isophthalic acid (IA), and terephthalic acid (TA), 2,5-pyridinedicarboxylic acid, 2,4-pyridinedicarboxylic acid, 3,5-pyridinedicarboxylic acid, 2,2-bis(4-carboxyphenyl)propane, bis(4-carboxyphenyl)methane, 2,2-bis(4-carboxyphenyl)hexafluoropropane, 2,2-bis(4-carboxyphenyl)ketone, bis(4-carboxyphenyl)sulfone, 2,2-bis(3-carboxyphenyl)propane, bis(3-carboxyphenyl)methane, 2,2-bis(3-carboxyphenyl)hexafluoropropane, 2,2-bis(3-carboxyphenyl)ketone, bis(3-carboxyphenoxy)benzene, naphthalene dicarboxylic acids, including 2,6-naphthalene dicarboxylic acid, 2,7-naphthalene dicarboxylic acid, 1,4-naphthalene dicarboxylic acid, 2,3-naphthalene dicarboxylic acid, 1,8-naphthalene dicarboxylic acid. Among acids (AL), mention can be notably made of oxalic acid (HOOC—COOH), malonic acid (HOOC—$CH_2$—COOH), succinic acid [HOOC—$(CH_2)_2$—COOH], glutaric acid [HOOC—$(CH_2)_3$—COOH], 2,2-dimethyl-glutaric acid [HOOC—$C(CH_3)_2$—$(CH_2)_2$—COOH], adipic acid [HOOC—$(CH_2)_4$—COOH], 2,4,4-trimethyl-adipic acid [HOOC—$CH(CH_3)$—$CH_2$—$C(CH_3)_2$—$CH_2$—COOH], pimelic acid [HOOC—$(CH_2)_5$—COOH], suberic acid [HOOC—$(CH_2)_6$—COOH], azelaic acid [HOOC—$(CH_2)_7$—COOH], sebacic acid [HOOC—$(CH_2)_8$—COOH], undecanedioic acid [HOOC—$(CH_2)_9$—COOH], dodecanedioic acid [HOOC—$(CH_2)_{10}$—COOH], tetradecanedioic acid [HOOC—$(CH_2)_{12}$—COOH], octadecanedioic acid [HOOC—$(CH_2)_{16}$—COOH], 2,5-furandicarboxylic acid and tetrahydrofuran-2,5-dicarboxylic acid. Preferably, the acid (DA) used for the manufacture of the polyamide (A) will be an acid (AL), as above detailed. Preferred examples of acids (AL) are adipic acid and sebacic acid.

Among suitable aminoacids (AN) for the manufacture of polyamide (PA), mention can be made of those selected from the group consisting of 6-amino-hexanoic acid, 9-aminononanoic acid, 10-aminodecanoic acid, 11-aminoundecanoic acid, 12-aminododecanoic acid.

Among suitable aminoacids suitable lactams (L) for the manufacture of polyamide (PA), mention can be made of β-lactam and ε-caprolactam.

(PFPE-DA) is a fluoropolymer comprising a fully or partially fluorinated polyalkyleneoxy chain [(per)fluoropolyoxylakylene chain ($R_f$)] having two chain ends, wherein each chain end comprises a —COOH group or a derivative thereof as defined above, preferably an ester or a halide.

(PFPE-NN) is a fluoropolymer comprising a fully or partially fluorinated polyalkyleneoxy chain [(per)fluoropolyoxylakylene chain ($R_f$)] having two chain ends, wherein each chain end comprises an amino group or a derivative thereof as defined above.

Chain ($R_f$) comprises, preferably consists of, recurring units R° having at least one catenary ether bond and at least one fluorocarbon moiety, said repeating units, randomly distributed along the chain, being selected from the group consisting of:
(i) —CFXO—, wherein X is F or $CF_3$;
(ii) —$CF_2$CFXO—, wherein X is F or $CF_3$;
(iii) —$CF_2CF_2CF_2O$—;
(iv) —$CF_2CF_2CF_2CF_2O$—.

More preferably, chain $R_f$ comprises, preferably consists of, recurring units R°:
(i) —$CF_2O$— and
(ii) —$CF_2CF_2O$—
wherein the molar ratio between recurring units (ii) and (i) ranges from 0.1 to 10, preferably from 0.5 to 5.

For the sake of accuracy, (PFPE-DA) and (PFPE-NN) to be used according to the present invention identify mixtures containing small amounts of the corresponding non-functional PFPE and/or PFPE monocarboxylic acid or PFPE monoamine. Such mixtures have an average functionality (F) of at least 1.80, preferably of at least 1.95. Average functionality (F) is defined as:

[2×moles of (PFPE-DA) or (PFPE-NN)+1×moles of PFPE monocarboxylic acid or monoamine)/
(moles of non-functional PFPE+moles of PFPE monocarboxylic acid or monoamine+moles of PFPE dicarboxylic acid or diamine].

(PFPE-DA) and (PFPE-NN) preferably comply with general formula (I) here below:

$$A\text{-}O\text{—}R_f\text{-}A' \qquad (I)$$

wherein:
$R_f$ is as defined above;
A and A' represent groups of formula:

$$CF_2\text{-}L_x\text{-}T$$

in which:
L represents a bivalent radical selected from:
(a) a $C_1$-$C_{20}$ straight or branched $C_3$-$C_{20}$ alkylene chain ($C_{alk}$), optionally containing one or more heteroatoms selected from O, N, S and P and/or one or more groups of formula —C(O)—, —C(O)O—, —OC(O)O—, —C(O)NH—, —NHC(O)NH— and —C(O)S—, said chain optionally containing a (heterocyclo)aliphatic ring ($R_{ali}$) or (heterocycloaromatic) ring ($R_{ar}$) as defined herein below;
(b) a $C_3$-$C_{10}$ cycloaliphatic ring ($R_{ali}$), optionally substituted with one or more straight or branched alkyl groups, preferably $C_1$-$C_3$ alkyl groups, and optionally containing one or more heteroatoms selected from N, O, S or groups of formula —C(O)—, —C(O)O— and —C(O)NH; the cycloaliphatic ring can also be linked to or condensed with a further ring ($R_{ali}$) or with a $C_5$-$C_{12}$ aromatic or heteroaromatic ring ($R_{ar}$) as defined herein below, which can optionally be substituted with one or more straight or branched alkyl groups, preferably $C_1$-$C_3$ alkyl groups;
x is 0 or 1;
(c) a $C_5$-$C_{12}$ aromatic ring ($R_{ar}$), optionally containing one or more heteroatoms selected from N, O, S and optionally being substituted with one or more straight or branched alkyl groups, preferably $C_1$-$C_3$ alkyl groups; optionally, ring ($R_{ar}$) can be linked to or condensed with another equal or different ring ($R_{ar}$);
T is —COOH or —$NH_2$ group or a derivative thereof as defined above.

Typically, in (PFPE-DA) and (PFPE-NN) of formula (I) above, x is 1 and linking group L comprises one of the following groups W, said group W being directly bound to the —$CF_2$— group between chain ($R_f$) and linking group L: —$CH_2O$—, —$CH_2OC(O)NH$—, —$CH_2NR^1$— in which $R^1$ is hydrogen or straight or branched $C_1$-$C_3$ alkyl, and —C(O)NH—.

It has indeed been observed that (PFPE-DA) and (PFPE-NN) wherein x is 1 are advantageous in that they are particularly reactive and compatible with amines (NN) and acids (DA) and in that they are also thermally and chemically stable under the polymerization conditions used to prepare polyamides (PA).

Preferred examples of (PFPE-DA) and (PFPE-NN) are those wherein A and A' are selected from the following groups:

($a^1$) —$CF_2CH_2O$-alkylene-T;
($b^1$) —$CF_2CH_2O$(alkylene-O)$_n$—$C^*_{alk}$-T;
($c^1$) —$CF_2CH_2O$-alkylene-O(O)NH-alkylene-T;
($d^1$) —$CF_2CH_2NR^1$-alkylene-T;
($e^1$) —$CF_2CH_2NR^1$(alkylene-$NR^1$)$_n$—$C_{alk}$-T;
($f^1$) —$CF_2CH_2NR^1$-alkylene-C(O)O-alkylene-T;
($g^1$) —$CF_2CH_2NR^1$-alkylene-O(O)NH-alkylene-T;
($h^1$) —$CF_2C(O)NH$—($C^*_{alk}$)-T
($i^1$) —$CF_2C(O)NH$—($R^*_{ali}$)-T; and
($l^1$) —$CF_2C(O)NH$—($R^*_{ar}$)-T
wherein:
  alkylene is a $C_1$-$C_{20}$ straight or branched $C_3$-$C_{20}$ alkylene chain, preferably a $C_2$-$C_{12}$ chain;
  n is a positive number ranging from 1 to 10, preferably from 1 to 5, more preferably from 1 to 3, extremes included;
  T is as defined above;
  $R^1$ is hydrogen or straight or branched $C_1$-$C_3$ alkyl;
  $C^*_{alk}$, $R^*_{ali}$ and $R^*_{ar}$ have the same meanings as $C_{alk}$, $R_{ali}$ and $R_{ar}$ defined above.

In (PFPE-DA) and (PFPE-NN) wherein A and A' are groups of formula ($b^1$), preferred (alkylene-O) moieties include —$CH_2CH_2O$—, —$CH_2CH(CH_3)O$—, —$(CH_2)_3O$— and —$(CH_2)_4O$—.

(PFPE-DA) and (PFPE-NN) according to the present invention wherein x is 1 and L comprises a W group of selected from —$CH_2O$—, —$CH_2OC(O)NH$— and —$CH_2NR^1$— in which $R^1$ is hydrogen or straight or branched $C_1$-$C_3$ alkyl can be obtained using as precursor a PFPE diol of formula (II) below:

$$HOCH_2CF_2—O—R_f—CF_2CH_2OH \quad (II)$$

wherein $R_f$ is as defined above.

Suitable PFPE diols of formula (II) can be prepared by photoinitiated oxidative polymerization (photooxidation reaction) of per(halo)fluoromonomers, as described in U.S. Pat. No. 3,715,378 (MONTECATINI EDISON S.P.A.) Feb. 6, 1973 and U.S. Pat. No. 3,665,041 (MONTEDISON S.P.A.) May 23, 1972. Typically, mixtures of perfluoropolyethers can be obtained by combination of hexafluoropropylene and/or tetrafluoroethylene with oxygen at low temperatures, in general below −40° C., under U.V. irradiation, at a wavelength (A) of less than 3 000 Å. Subsequent conversion of end-groups as described in U.S. Pat. No. 3,847,978 (MONTEDISON S.P.A.) Nov. 12, 1974 and in U.S. Pat. No. 3,810,874 May 15, 1974 is notably carried out on crude products from photooxidation reaction.

(PFPE-DA) and (PFPE-NN) wherein W is —$CH_2O$— can be obtained by reaction of PFPE diol (II) with a compound of formula E-$B^*$-T, wherein E represents a leaving group, $B^*$ represents a group selected from $C^*_{alk}$, $R^*_{ali}$ and $R^*_{ar}$ and T is amino or carboxy, optionally in a protected form. Suitable leaving groups E include halogens, preferably chlorine and bromine, and sulfonates like trifluoromethanesulfonate. Preferred protecting groups for —COOH groups are esters, while preferred protecting groups for —$NH_2$ groups are amides and phthalimides. As an alternative, the terminal hydroxy groups in the PFPE diol of formula (I) can be transformed into leaving groups E as defined above and reacted with a compound of formula HO—$B^*$-T wherein $B^*$ and T are as defined above.

Typically, (PFPE-DA) and (PFPE-NN) wherein A and A' represent groups of formula ($a^1$) as defined above can be obtained by reaction of a PFPE diol (II) with a compound of formula E-$C^*_{alk}$-T, wherein E, $C^*_{alk}$ and T are as defined above. A preferred example of (PFPE-DA) wherein group ($a^1$) is —$CF_2CH_2O$—$CH_2$-T can be obtained by reaction of a PFPE-diol (II) with an ester of a 2-halo-acetic acid, for example with 2-chloroethyl acetate.

(PFPE-PA) and (PFPE-NN) wherein A and A' represent groups of formula ($b^1$) as defined above can be synthesised by condensation reaction of a PFPE diol (II) with a diol of the type HO-alkylene-OH or by ring-opening reaction of a PFPE diol (II) with ethylene oxide or propylene oxide, to provide a hydroxyl compound which is either reacted with compound of formula E-$C^*_{alk}$-T or submitted to conversion of the hydroxyl end groups into leaving groups E as defined above and reacted with a compound of formula HO—$C^*_{alk}$-T.

(PFPE-DA) and (PFPE-NN) wherein A and A' represent groups ($c^1$) as defined above can be synthesised by reaction of a (PFPE-DA) wherein A and A' represent groups —$CF_2CH_2O$-alkylene-T with a diamine or aminoacid of formula $NH_2$-alkylene-T, wherein alkylene and T are as defined above.

(PFPE-DA) and (PFPE-NN) wherein x is 1 and L comprises a W group of formula —$CH_2NHR^1$— in which $R^1$ is as defined above can be obtained by reaction of a PFPE diol (II), whose hydroxyl end groups E have been transformed into leaving groups E, with a compound of formula $R^1$HN—$B^*$-T wherein $R^1$, $B^*$ and T are as defined above.

For example, a (PFPE-DA) or a (PFPE-NN) wherein A and A' represent groups of formula ($d^1$) as defined above can be synthesised by reaction of a PFPE diol (II) with an amine of formula $R^1$NH-alkylene-T, wherein $R^1$ and alkylene are as defined above and wherein T is optionally in a protected form.

A (PFPE-DA) or (PFPE-NN) wherein A and A' represent groups of formula ($e^1$) as defined above can be synthesised by reaction of a PFPE diol (II) with a polyamine of formula $R^1$NH-(alkylene-$NR^1$)$_{n-1}$alkylene-$NHR^1$, followed by reaction with a compound of formula E-$C^*_{alk}$-T, wherein E, C and T are as defined above.

A (PFPE-DA) or (PFPE-NN) wherein A and A' represent groups of formula ($f^1$) as defined above can be synthesised by reaction of a PFPE diol (II) with an aminoacid of formula $R^1$NH-alkylene-T, followed by reaction with a compound of formula HO-alkylene-T, wherein T is as defined above. A (PFPE-DA) or (PFPE-NN) wherein A and A' represent groups of formula ($g^1$) as defined above can be synthesised by reaction of a PFPE diol (II) with an aminoacid of formula $R^1$NH-alkylene-COOH, followed by reaction with a compound of formula $NH_2$-alkylene-T.

As an alternative, (PFPE-DA) and (PFPE-NN) wherein x is 1 and L comprises a W group of formula —$CH_2NHR^1$— in which $R^1$ is as defined above can be obtained by converting a PFPE diol (II) into the corresponding sulfonic diester derivative, by reaction, for example, with $CF_3SO_2F$ and reacting the sulfonic diester with anhydrous liquid ammonia to provide a PFPE diamine of formula (III) below:

$$NH_2CH_2CF_2—O—R_f—CF_2CH_2NH_2 \quad (III)$$

wherein $R_f$ is as defined above.

PFPE diamine (III) can be reacted with a compound of formula E-$B^*$-T, wherein E, $B^*$ and T are as defined above.

(PFPE-DA) and (PFPE-NN) according to the present invention wherein x is 1 and L comprises a W group of formula —C(O)NH— can be obtained using as precursor a PFPE diacid of formula (IV) below:

$$HOOCCF_2—O—R_f—CF_2COOH \quad (IV)$$

in which $R_f$ is as defined above
or a reactive derivative thereof, preferably an ester derivative, typically a methyl or ethyl ester derivative.

Suitable PFPE ester derivatives of PFPE diacids (IV) can be conveniently obtained as disclosed, for example, in U.S. Pat. No. 5,371,272 (AUSIMONT SPA).

PFPE diacids (IV) or reacted derivatives thereof can be reacted with compounds of formula $N_2H-B^*-T$, wherein $B^*$ and T are as defined above.

In particular, (PFPE-DA) and (PFPE-NN) according to the present invention wherein A and A' comply with formulae $(h^1)-(l^1)$ as defined above can be prepared by reaction of an ester derivative of a diacid (III) with a compound of formula $NH_2-(C^*_{alk})-T$, $NH_2-(R^*_{ali})-T$ or $NH_2-(R^*_{ar})-T$.

For the sake of clarity and accuracy, it is pointed out that, in certain instances, the synthesis of (PFPE-DA) and (PFPE-NN) of formula (I) above can lead to the formation of a certain amount of by dimeric or polymeric products; for example, in the synthesis of a (PFPE-NN) wherein A and A' represent groups of formula:

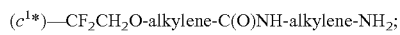

$(c^{1*})-CF_2CH_2O$-alkylene-$C(O)NH$-alkylene-$NH_2$;

dimeric by products of formula:

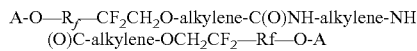

A-O-$R_f$-$CF_2CH_2O$-alkylene-$C(O)NH$-alkylene-NH(O)C-alkylene-$OCH_2CF_2$-Rf-O-A are obtained, due to the reaction of a diamine of formula: $H_2N$-alkylene-$NH_2$ with diacid of formula: $HOOC$-alkylene-O-$CH_2CF_2$-O-$R_f$-$CF_2CH_2O$-alkylene-COOH in a molar amount of 1 to 2.

Furthermore, in the synthesis of (PFPE-NN) obtained by reaction of a PFPE diol with an amine of formula $R^1NH$-alkylene-$NH_2$ in which $R^1$ is other than hydrogen, mixtures of regioisomers of formulae:

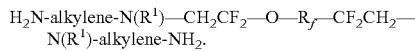

$H_2N$-alkylene-$N(R^1)$-$CH_2CF_2$-O-$R_f$-$CF_2CH_2$-$N(R^1)$-alkylene-$NH_2$.

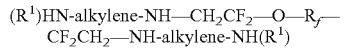

$(R^1)HN$-alkylene-NH-$CH_2CF_2$-O-$R_f$-$CF_2CH_2$-NH-alkylene-$NH(R^1)$ can be obtained.

Thus, for the purposes of the present invention, the expressions "PFPE DA" and "PFPE NN" is intended to comprise also any dimeric or polymeric by-products or regioisomers which may be formed in the process for their preparation.

Furthermore, for the purposes of the present invention, a polyamide (PA) is intended to denote a polyamide obtained by using a (PFPE-DA) or a (PFPE-NN) and their dimeric or polymeric by-products, where present.

Polyamides (PA) according to the present invention can be conveniently synthesised by means of a process (or method) which comprises reacting a monomers (A) and (B) as defined above according to known methods for the synthesis of polyamides. According to a first embodiment, monomers (A) and (B) are contacted as such, i.e. without solvents, in a reaction vessel and heated at temperatures typically ranging from 240° C. to 280° C. According to a second embodiment, a solvent is used; non-limiting examples of solvents include fluorinated solvents, like fluorinated aromatic hydrocarbons, optionally in admixture with non-fluorinated organic solvents. Once the desired viscosity is reached, the molten polymer is quenched into cold water. It has been noted that under conditions typical for the synthesis of polyamides, monomer (B), i.e. (PFPE-M), is incorporated in the PA chain through covalent amido bonds.

Thanks to the presence of recurring units derived from (PFPE-M) in amounts of from 0.1 to 10%, preferably from 1% to 5% with respect to recurring units derived from monomers (A) and (B), polyamides (PA) according to the present invention retain their thermoplastic behaviour, but they show improved hydro- and oleo-phobicity with respect to non-modified polyamides. Furthermore, the (PA) of the invention are endowed with higher chemical resistance and show lower wear- and friction-coefficient. For these reason, polyamides (PA) according to the invention have higher durability.

The thermoplastic (PA) of the invention can be used, for example, in the manufacture of formed articles for a variety of consumer and industrial applications, like automotive, electrical and electronic applications or in the manufacture of packagings. Polyamides (PA) can be used alone or in admixture with one another; moreover, one or more polyamide (PA) can be used as such or they can be blended with further ingredients and/or additives to obtain (PA) compositions. Accordingly, the present invention relates to formed articles containing one or more polyamide PA or a composition comprising one or more polyamide (PA) in admixture with further ingredients and additives. Non-limiting examples of further ingredients and/or additives include heat-stabilizers, light and UV-light stabilizers, hydrolysis stabilizers, anti-oxidants, lubricants, plasticizers, colorants, pigments, antistatic agents, flame-retardant agents, nucleating agents, catalysts, mold-release agents, fragrances, blowing agents, viscosity modifiers, flow aids, glass fibers and the like. The kind and amount of ingredients and/or additives will be selected by the skilled person according to common practice, for example following the teaching of *Plastics Additives Handbook*, 5th ed., Hanser, 2001.

According to a preferred embodiment, the compositions comprise one or more polyamide (PA) in admixture with glass fibers. Typically, such composition comprise from 10% to 70% wt with respect to the weight of the composition. The Applicant observed that compositions comprising one or more polyamides (PA) according to the present invention, in particular those comprising a (PFPE-DA), and glass fibers can be used for the manufacture of formed articles having significantly higher hydro- and oleo-phobicity, higher tensile strength, higher strain at break and also higher impact strength than compositions comprising polyamides obtained without using any (PFPE-DA) or (PFPE-NN).

The invention further relates to a method for manufacturing formed articles comprising polyamides (PA) or compositions of polyamides (PA), said method comprising:
- melting one or more polyamide (PA) or a composition of a polyamide (PA) to obtain a molten polyamide (PA) or molten polyamide composition;
- casting the molten (PA) or (PA) composition into a mold and
- cooling.

Non limiting examples of formed articles include fuel line hoses, miniature circuit breakers (MCB), electrical switches and smart devices.

Thanks to the use of polyamides (PA), the formed articles are endowed with improved hydro-/oleo-phobicity, improved thermal and chemical resistance and reduced brittleness.

Should the disclosure of any patents, patent applications, and publications which are incorporated herein by reference conflict with the description of the present application to the extent that it may render a term unclear, the present description shall take precedence.

The invention will be herein after illustrated in greater detail in the following experimental section.

EXPERIMENTAL SECTION

1. Materials and Methods

Fluorolink® D10H PFPE, characterized by the following structure:

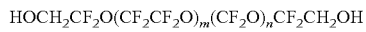

(m/n=2.5; MW 1,500), available from Solvay Specialty Polymers was used as received.

m-xylylene diamine was purchased from Mitsubishi Gas Chemical Company, Inc. Japan and was used as received.

Adipic acid was purchased from Loba Chemie PVT LTD and used as received.

Sebacic acid was purchased from Biotor Industries Ltd. and used as received.

1H-NMR, $^{19}$F-NMR and $^{13}$C-NMR spectra were recorded on a Varian Mercury 300 MHz instrument.

IR spectra were recorded on a Nicolet Avatar 360 FTIR-ESP instrument interfaced with OMNIC software.

Contact angle measurements were carried out with a Dataphysics Contact Angle System OCA 20 instrument. Contact angle measurements were used to confirm the present of fluorine in the polyamide samples.

2. Synthesis Examples

3. Synthesis of (PFPE-DA) and (PFPE-NN)

EXAMPLE 1

Synthesis of an ethyl ester of a (PFPE-DA) of formula:

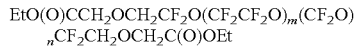

(m/n=2.5; MW: 1,793; EW: 896)

40 g t-But-OH and 19 g (170 meq) t-BuOK were charged in a ½ l reactor, then 100 g (130 meq) Fluorolink® D10H was added under stirring at room temperature.

The reaction mass was maintained under these conditions for 30'; then 19.7 g (170 meq) ClCH$_2$C(O)OEt was added and internal temperature was raised to 80° C. for 12 hours. Thereafter, the reaction mass was cooled down to room temperature and 200 ml water containing 10% by weight 37% HCl was added, to obtain two phases. The two phases were separated and the bottom one was dried, to provide 104 g title product. $^1$H-NMR and IR analysis confirmed the structure reported in the title. $^1$H-NMR: 4.2 (—CH$_2$α to the —CF$_2$); 3.95 (—CH$_2$α to the carbonyl group).

EXAMPLE 2

Synthesis of a (PFPE-NN) of formula:

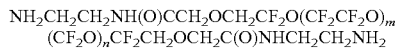

(m/n=2.5; MW: 1,829; EW: 910)

The ethyl ester of Example 1 (20 g, 22 meq) was charged in a reactor under inert atmosphere. 5.3 g (88 meq) ethylene diamine was added and the reaction mass was heated at 80° for 2 hours. IR analysis confirmed, by the disappearance of the ester carbonyl stretching, the completion of the amidation reaction. The excess of ethylene diamine was removed by vacuum distillation at 80° C. $^1$H-NMR confirmed structure reported in the title:

$^1$H-NMR: 4.2 (—CH$_2$ α to the —CF$_2$); 3.95 (—CH$_2$ α to the carbonyl group); 3.4 (—CH$_2$ α to the NH); 2.5 (—CH$_2$ α to the —NH$_2$).

EXAMPLE 3

Synthesis of a (PFPE-NN) of formula:

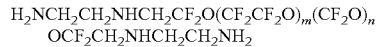

(m/n=1.2; EW=1,651 g/eq)

A 4-necked glass reactor equipped with a water-cooled condenser, a magnetic stirring bar and a dropping funnel was kept under inert atmosphere (N$_2$) by flowing N$_2$ for 20 min. The reactor was maintained under a static inert atmosphere by means of a nitrogen-filled balloon kept atop the condenser. The reactor was then loaded with 65.7 g (73 ml; 2.19 eq) ethylene diamine. Keeping the temperature at 20° C., 50 g PFPE nonaflate (43.8 meq; 22.18 mmoles; average MW=2,254 g/mol; average EW=1141 g/eq), prepared from a commercial Fomblin® Z DOL PFPE having MW=1,588; EW=827; functionality 1.82, were dropped in 145 min. with vigorous stirring (1100 rpm). The crude mixture was kept at 20° C. and at 1100 rpm for further 4 hrs. The progress of the reaction was followed by monitoring the amount of C$_4$F$_9$SO$_3^{(-)(+)}$H$_3$NC$_2$H$_4$NH$_3^{(+)(-)}$O$_3$SC$_4$F$_9$ in the upper ethylene diamine layer. Once complete, the crude reaction mixture was placed in a separating funnel and the lower PFPE layer was collected. The lower layer was then distilled under high vacuum at 70° C. and 5.3×10$^{-1}$ residual atm in order to eliminate residual ethylene diamine which partitioned in the lower PFPE layer, obtaining 35 g of paleyellow, clear oil. $^1$H-NMR and IR analyses confirmed the structure reported in the title, in admixture with 9% mol of dimeric by-products.

Isolated yield=83 mol %.

MW (GPC and NMR)=3,119 g/mol; EW=1,580 g/eq

PFPE dimer/monomer selectivity=91/9 in moles ethylene diamine and PFPE diol (Fomblin® Z-DOL PFPE resulting from hydrolysis of the nonaflate) absent or under the detectable limit.

TGA: 0% wt loss up to 150° C.; 16.6 wt % loss between 150°-300° C.

$^1$H-NMR (neat): 4.3 (—CF$_2$—<u>CH$_2$</u>—NH—); 3.9 (—NH—<u>CH$_2$CH$_2$</u>NH— of dimer); 3.8 (—NH<u>CH$_2$CH$_2$</u>NH$_2$); 2.8 (—NH—+—NH$_2$).

$^{19}$F-NMR (neat): −78+−80 (PFPE-<u>OCF$_2$</u>—CH$_2$—NR$_h$)

$^{13}$C-NMR (neat): 134-106 (PFPE); 52 (—OCF$_2$<u>CH$_2$</u>—); 50 (—NH<u>CH$_2$</u>CH$_2$—); 46 (—NH<u>CH$_2$</u>CH$_2$NH— dimer); 38 (—<u>CH$_2$</u>NH$_2$).

EXAMPLE 4

Synthesis of a mixture of (PFPE-NN) of formula:

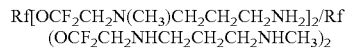

wherein Rf represents (CF$_2$CF$_2$O)$_m$(CF$_2$O)$_n$ with m/n=1.09 and EW=1,380 g/eq N-methyl-propyldiamine (97.59 grams, 1.109 moles; 116 ml) was placed in the same equipment under the same reaction conditions as described in Example 3. The same PFPE nonaflate as used in example 3 (50 g; 43.8 meq; 22.18 mmoles) was dropped in 155 min. with vigorous stirring (1200 rpm). The crude mixture was let to stir for further 5 hrs after the addition of the PFPE nonaflate. Once the reaction was complete (quantification of the nonaflate salt by NMR as described in Example 3), the crude mixture was separated in a separating funnel and the lower PFPE layer was distilled at 80° C. and 0.2 residual atm. The distillate was treated with 1% by wt active charcoal at 20° C. and filtered on a pressure filter with a 0.2 μm PFPE membrane, to afford 34.7 grams of pale-yellow, clear oil. NMR and IR analyses confirmed the structure reported in the title in admixture with dimeric by-products.

Isolated yield=85.5 mol %.
MW (GPC and NMR)=2,649 g/mol; EW=1,380 g/eq
PFPE Dimer/Monomer selectivity=47/53 in moles.
Regioselectivity —OCF$_2$CH$_2$N[CH$_3$](CH$_2$)$_3$NH$_2$/—OCF$_2$CH$_2$NH(CH$_2$)$_3$NHCH$_3$=36/64
N-methyl propyldiamine and Fomblin® Z-DOL PFPE (resulting from hydrolysis of the nonaflate) absent or under detectable limits.
TGA: 0% wt loss up to 150° C.; 10 wt % loss between 150°-236° C.; 20% wt. Loss up to 280° C.
$^1$H-NMR (neat): 3.5, 3.6 (—CF$_2$—CH$_2$—N—); 3.2 [—N(H)—CH$_2$CH$_2$CH$_2$N(H)— of dimer]; 3.3 (—N(CH$_3$)—CH$_2$—); 3.1 (—CH$_2$NH—); 2.9, 2.87 (—N(CH$_3$)—); 2.1 (—CH$_2$—+—NH$_2$+—NH—).
$^{19}$F-NMR (neat): −72+−73.7; −74.4+−75.5 (PFPE-OCF$_2$—CH$_2$—N)
$^{13}$C-NMR (neat): 134-106 (PFPE); 61 (—OCF$_2$CH$_2$—N(CH$_3$)—); 53.5 (—OCF$_2$CH$_2$NH—); 48+31 [—N(CH$_3$)(CH$_2$)$_3$NH—].

EXAMPLE 5

Synthesis of a (PFPE-NN) of formula:

Rf[OCF$_2$CH$_2$NH(CH$_2$)$_6$NH$_2$]$_2$ wherein Rf represents (CF$_2$CF$_2$O)$_m$(CF$_2$O)$_n$ with m/n=1.09 and EW=2430 g/eq)

Hexamethylene diamine (121 g, 1.042 moles, 136 ml) was placed in the same equipment as described in Example 3 and the mixture was heated to 60° C. PFPE nonaflate of commercial Fomblin® Z DOL PFPE (47 g; 41.89 meq; 20.85 mmoles; average MW=2,254 g/mol; average EW=1,141 g/eq) were dropped in 400 min. with vigorous stirring (1200 rpm), maintaining the reaction temperature at 60° C. The crude mixture was let to stir for further 8 hrs after the addition of the PFPE nonaflate. Once the reaction was complete (quantification of the nonaflate salt by NMR as described in Example 3) the crude mixture was first diluted in 60 ml CH$_2$Cl$_2$, in order to prevent unreacted hexamethyldiamine to solidify (f.p.=45° C.) and then poured in a separating funnel. The lower phase was collected and then distilled at 80° C. and 0.52 residual atm. obtaining 31 grams of a pale-yellow oil. NMR and IR analyses confirmed the structure reported in the title, in admixture with dimeric and trimeric by-products.

Isolated yield=78.8 mol %.
MW (GPC and NMR)=4,803 g/mol; EW=2,430 g/eq
PFPE Dimer/Trimer selectivity=53/47 in moles.

Hexamethyldiamine and Fomblin® Z-DOL PFPE (resulting from hydrolysis of the nonaflate) absent or under detectable limits.
TGA: 0% wt loss up to 200° C.; 10 wt % loss between 200°-312° C.
$^1$H-NMR (neat): 4.5, (—CF$_2$—CH$_2$—N—; dimer+trimer); 4.1 (—CH$_2$NHX; X=H, —CH$_2$—); 2.9-2.6 (—[CH$_2$—]$_4$; —NH—; —NH$_2$).
$^{19}$F-NMR (neat): −75+−78; (PFPE-OCF$_2$—CH$_2$—N)
$^{13}$C-NMR (neat): 134-106 (PFPE); 53.5 (—OCF$_2$CH$_2$NH—); —NH$^f$CH$_2^e$CH$_2^d$ CH$_2^c$CH$_2^b$CH$_2^a$NH$_2$; —NH$^1$CH$_2^2$CH$_2^3$CH$_2^3$CH$_2^2$CH$_2^1$CH$_2$NH—: 50.5 (f+1); 43.5 (a); 35 (b); 31.5 (e+2); 28 (c+d+3).

EXAMPLE 6

Synthesis of a (PFPE-DA) of Formula

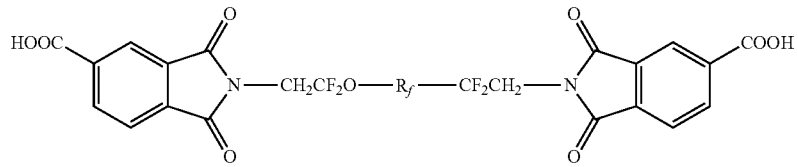

wherein Rf represents (CF$_2$CF$_2$O)$_m$(CF$_2$O)$_n$ with m/n=1.79 and Ew=EW=790 g/eq In the same apparatus as described in Example 3, 1,2,4-tricarboxylic anhydride (37.3 g; 0.1944 moles) was dissolved in 140 ml anhydrous DMF to obtain a homogeneous reaction mixture, which was heated to 100° C. and stirred at 900 rpm. Thereafter, a (PFPE NN) of formula A-O—R$_f$-A' (60 g; 35.2 mmoles; 64.8 meq; wherein R$_f$ represents (CF$_2$CF$_2$O)$_m$(CF$_2$O)$_n$, A and A' represent —CF$_2$CH$_2$NH$_2$ and in which m and n are selected in such a way as the average MW is 1,704 g/mole and the average EW is 926 g/eq) was added in approximately 25 min, to obtain a slightly opaque mixture. The mixture was then heated to 136° C. for 6 hrs and then to 155°-160° C. for further 10 hrs. The resulting crude mixture was cooled to 25° C. and extracted with 200 ml of Galden® HT-110 PFPE. Two clear-cut layers separated. The desired product, along with DMF and traces of Galden® HT-110 PFPE was in the top layer. The top layer was then extracted with 200 ml of distilled H$_2$O and a white solid precipitated. Upon addition of CH$_2$Cl$_2$, a fraction of the solid remained undissolved and it was identified (NMR) as unreacted 1,2,4-tricarboxilic anhydride. The CH$_2$Cl$_2$ solution was extracted with H$_3$O$^{(+)}$ Cl$^{(−)}$ (2:1 vol); a waxy, white solid precipitated which was scarcely soluble in Freon/acetone. This product was identified (NMR) as a polyamide resulting from the reaction between PFPE diamine and the 4-carboxylic group of the anhydride or of the target product. The purified CH$_2$Cl$_2$ phase is evaporated obtaining 62 grams of a dense oil which crystallized overnight at 20° C. IR and NMR analyses confirmed the structure reported in the title: Isolated yield=63.4 mol %

MW=1,510 g/mol; EW=790 g/eq.
TGA: 20% wt loss at 200° C.; 50% wt loss at 300° C. due to the —COOH moiety.

EXAMPLE 7

Synthesis of a (PFPE-NN) of formula:

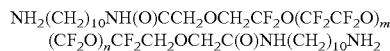

NH$_2$(CH$_2$)$_{10}$NH(O)CCH$_2$OCH$_2$CF$_2$O(CF$_2$CF$_2$O)$_m$(CF$_2$O)$_n$CF$_2$CH$_2$OCH$_2$C(O)NH(CH$_2$)$_{10}$NH$_2$ (m/n=2.5; MW: =1,990; EW=1,010)

The PFPE-diester derivative of example 1 was reacted with a 5 molar excess of 1,10-diaminodecane (C$_{10}$-diamine) by heating the two reagents neat in a round bottom flask fitted under nitrogen at a temperature of 110° C. The progress of the reaction was monitored for complete disappearance of the diester by FT-IR, which typically took 16-24 h. The excess of 1,10-diaminodecane was allowed to sublime by heating the reaction mixture to about 100° C. over a period of several hours and the sublimed amine was separated manually from the cold reactor spots. FT-IR and $^1$HNMR analyses confirmed the structure reported in the title.

4. Synthesis of Polyamides (PA)

EXAMPLE 8 (COMPARATIVE EXAMPLE)

Synthesis of MXD10

Sebacic acid (1 mol, 202 g) was charged in a 500 mL glass kettle attached with kettle head fitted with four ground joints having a T-joint adapter, thermometer pocket, thermometer, anchor type overhead stirrer, water condenser and a receiver round bottom flask. The kettle was flushed with nitrogen and submerged in an oil bath and the temperature was raised gradually so as to melt the acid (m.p.=134.5° C.). When the acid was completely in molten form, it looked transparent. Stirring was further continued at 50 rpm using an overhead stirrer. MXDA (m-xylenediamine, 1 mol, 136 g) was added drop wise through an addition funnel in such a way that addition lasted for 45-60 min. During this time, the temperature was raised to 210° C. The salt formation initiated and water started to distil out. When water generation ceased, the temperature of the oil bath was raised to 250° C. When the desired torque was built up, stirring was stopped, setup unassembled and the molten polymer was poured and quenched in an ice-cold water bath.

EXAMPLE 9

Polyamide MXD10 Containing 5% w/w of the (PFPE-NN) of Example 7

A procedure similar to that described in Example 8 was followed, except that once the sebacic acid was completely in the molten form, the (PFPE-NN) of Example 7 was added to the kettle in order to reach a final PFPE concentration in the polymer of 5% (w/w). The mixture was then allowed to mix thoroughly. After 30 min of mixing, MXDA (m-xylylenediamine) was added dropwise and the reaction was continued as indicated in Example 8. $^1$H-NMR, $^{13}$C-NMR and $^{19}$F-NMR analyses confirmed that the desired polyamide was obtained. The disappearance of signals at δ 41.1 and δ 39.8 due to —PFPE-CF$_2$—CH$_2$—O—CH$_2$—CONHCH$_2$(CH$_2$)$_8$CH$_2$NH$_2$ and the appearance of a single signal at δ 40.1 due to —PFPE-CF$_2$—CH$_2$—O—CH$_2$—CONHCH$_2$(CH$_2$)$_8$CH$_2$NHCO(CH$_2$)$_8$—CO— due to amidation of PFPE-NN with sebacic acid in $^{13}$C-NMR confirmed that the (PFPE-NN) was covalenty bound in the polyamide. Fluorine estimation by combustion ion chromatoraphy indicated that the fluorine content was 1.6% w/w (vs a theoretical value 2.5%).

EXAMPLE 10

Synthesis of Polyamide MXD10 Containing 2% w/w of the (PFPE-NN) of Example 7

Similarly to what described in Example 8, a polyamide (PA) comprising blocks of sebacic acid, MXDA and 2% w/w of (PFPE-NN) of Example 7 was obtained. $^1$H-NMR, $^{13}$C-NMR and $^{19}$F-NMR analyses confirmed that the desired polyamide was obtained, and that the PFPE diamine was covalently bound in the polyamide. Fluorine estimation by combustion ion chromatography indicated that the fluorine content was 0.8% w/w (vs a theoretical value of 1.2%).

EXAMPLE 11

Synthesis of Polyamide MXD10 Containing 1% w/w of (PFPE-NN) of Example 7

Similarly to what described in Example 8, a polyamide (PA) comprising blocks of sebacic acid, MXDA and 1% w/w of (PFPE-NN) of Example 7 was obtained. $^1$H-NMR, $^{13}$C-NMR and $^{19}$F-NMR analyses confirmed that the desired polyamide was obtained, and that the PFPE diamine was covalently bound in the polyamide. Fluorine estimation by combustion ion chromatography indicated that the fluorine content was 0.4% w/w (vs a theoretical value 0.5%).

EXAMPLE 12 (COMPARATIVE EXAMPLE)

Synthesis of Polyamide MXD6

Polyamide of MXD6 was synthesised from adipic acid and MXDA, following a procedure similar to that of Example 8, with the difference that adipic acid and MXDA were added one pot and the temperature was raised to about 275° C.

EXAMPLE 13

Synthesis of Polyamide MXD6 Containing 2% w/w of PFPE NN of Example 7

The procedure of Example 12 was followed, with the difference that a solution of the (PFPE-NN) of Example 7 in hexafluoroxylene (HFX) and methanol (MeOH) was also added. The amount of (PFPE-NN) in the solution was calculated in order to reach a final amount of (PFPE-NN) block in the polyamide of 2% w/w. The solvents and water were distilled out during the course of the reaction and the polyamide was isolated as described above. $^1$H-NMR, $^{13}$C-NMR and $^{19}$F-NMR confirmed the desired polyamide (PA) was obtained, and that the (PFPE-NN) was covalently bound in the polyamide. Fluorine estimation by combustion ion chromatography indicated that the fluorine content was 0.8% w/w (vs a theoretical value of 1.2%).

EXAMPLE 14

Synthesis of Polyamide MXD6 Containing 1% w/w of (PFPE-NN) of Example 7

The procedure of Example 13 was followed, with the difference that the amount of (PFPE-NN) of Example 7 in the solution was calculated in order to reach a final amount of (PFPE-NN) block in the polyamide of 1% w/w. $^1$H-NMR, $^{13}$C-NMR and $^{19}$F-NMR analyses confirmed that the desired polyamide was obtained, and that the (PFPE-NN) was covalenty bound in the polyamide. Fluorine estimation by combustion ion chromatography indicated that the fluorine content was 0.4% w/w (vs a theoretical value of 0.5%).

EXAMPLES 15

Synthesis of Polyamide MXD6 Containing 2% w/w of PFPE DA of Example 1

The procedure of Example 12 was followed, with the difference that the PFPE-diester derivative of Example 1 was added without solvents in an amount of 2% w/w with respect to adipic acid and MXDA

EXAMPLES 16

Synthesis of Polyamide MXD6 Containing 2% w/w of (PFPE-NN) of Example 2

The procedure of Example 13 was followed, with the difference that the amount of (PFPE-NN) of Example 2 was calculated in order to reach a final amount of (PFPE-NN) block in the polyamide of 2% w/w. $^1$H-NMR, $^{13}$C-NMR and $^{19}$F-NMR analyses confirmed that the desired polyamide was obtained. Similarly as described in Example 9, signals at δ 41.9 and δ 44.7 in $^{13}$C-NMR confirmed that the (PFPE-NN) was covalently bound in the polyamide. Contact angle measurement showed the increase in hydrophobocity and oleo-phobicity (Table 1).

EXAMPLES 17a-17c

Synthesis of Polyamides MXD6 Containing 1, 3 and 5% of PFPE DA of Example 1

A stirred batch stained steel vessel (5 L capacity) was charged with adipic acid (4.44 mol, 648.9 g), m-xylenediamine (4.45 mol, 605.8 g) and PFPE-diester derivative of Example 1 (1 wt %, 0.0068 mol, 12.56 g) and closed. The mixture was blanketed with nitrogen and then heated up to 200° C. At this point of time, the internal pressure rose close to 4.5 kg and was kept constant for about an hour. During this step, the temperature was raised to 250° C. Afterwards, the vessel was depressurized gradually over a period of 30 min. The polymerization was continued for another 30 min under nitrogen atmosphere wherein the torque increased to the desired value. The final polymer melt was drawn from the bottom valve and quenched in ice cold water and pelletized.

EXAMPLE 18

Preparation of Compositions of PA Reinforced with Glass Fibers

MXD6 or the PA of Examples 17a-17c and glass fibre [OCV EC10 983 (4.5 mm)] were co-extruded in a ratio of 70:30 on a ZSK-26 twin screw extruder. The PA were fed to the first barrel of zone-1 of the extruder comprising of 12 zones via a loss in weight feeder. The barrel settings were in the range of 220-250° C. The glass fibre was fed from zone 7 through a side stuffier via a loss in weight feeder. The screw rate was 100 rpm. The extrudates were cooled and pelletized using a conventional equipment.

EXAMPLE 19

Preparation of Formed Articles by Injection Molding

The compositions prepared according to Example 18 were molded on a Sumitomo 75 TON injection molding machine. The temperature range was 265° C.-280° C. The mold temperature controller was set to 140° C.-165° C. The cooling cycle time was fixed to 35-50 sec. Under these setup conditions, ISO tensile test pieces, impact bars and colour plaques were molded.
Tests
Contact Angle Measurements
Table 1 summarizes the results of static contact angle measurements of the polyamides PA of Examples 8-16 vs water and n-hexadecane.

TABLE 1

| Static contact angle measurements of the PA of Ex 8-16 | | |
|---|---|---|
| Polymer | water | n-hexadecane |
| Ex 8 | 91.7 | 37.4 |
| Ex 9 | 109.4 | 69.5 |
| Ex 10 | 108.1 | 69.5 |
| Ex 11 | 109.3 | 69.2 |
| Ex 12 | 92.3 | 38.4 |
| Ex 13 | 115.8 | 69.3 |
| Ex 14 | 98.7 | 69.4 |
| Ex 15 | 102.4 | 68.8 |
| Ex 16 | 100.7 | 71.4 |

It is evident from the results reported in Table 1 that the polyamides according to the present invention show significantly higher contact angle values towards water and n-hexadecane than the polyamides of reference Examples 8 and 12. Therefore, the polyamides according to the invention are endowed with higher hydro- and oleo-phobicity.

In order to confirm that the PFPE DA or PFPE NN was covalently bound in the polyamides, the polyamides PAs according to the invention were heated in a mixture of hot hexafluoroxylene and methanol at reflux temperature for several hours. The residual polymers were then filtered, washed with solvent and dried under vacuum. Contact angles towards water and n-hexadecane of these residual polymers were measured; the results showed no significant changes with respect to the measurements carried out before the treatment.

Gel Permeation Chromatography (GPC) Analysis of MXD6 and of the PA of Examples 17a-17c MXD6 and the PA of Examples 17a-17c were completely dissolved in hexafluoroisopropanol (HFIPA) containing 0.05M potassium trifluoro acetate (KTFAT). Any fillers and insoluble additive were removed by filtration through 0.2 micron PTFE disposable syringe filters. The filtered PA solutions were separated on a size exclusion chromatography (SEC) system consisting of a Waters HPLC pump (model no. 515), Shodex refractive index (RI) detector (model no. 109), Waters column oven (capable for room temperature to 150° C.) maintained at 40° C. during the analysis, set of two mini mixed B SEC columns and mini mix B guard column (from Agilent), Clarity SEC integration software (Version 5.0.00.323). Mobile phase—HFIPA/ 0.05M potassium trifluoro acetate (KTFAT) at a flow rate of 0.4 mL/minute. The system was calibrated using the set of narrow polydisperse PMMA standard samples. Molecular weights were calculated using a calibration file generated using PMMA standards with the help of a Clarity SEC integration software. The results are reported in Table 2.

TABLE 2

GPC data of MXD6 and PA of Ex 17a-17c

| Polyamide | Mn | Mw | Mz | Mz1 | PDI* |
|---|---|---|---|---|---|
| MXD6 | 22903 | 54874 | 97186 | 151203 | 2.39 |
| PA of Ex 17a (containing 1% wt PFPE-DA) | 22959 | 55022 | 101024 | 164851 | 2.40 |
| PA of Ex 17b (containing 3% wt PFPE-DA) | 22994 | 56522 | 111346 | 196648 | 2.46 |
| Pa of Ex 17c (containing 5% PFPE-DA) | 21381 | 58658 | 122914 | 222514 | 2.74 |

*PDI = polydispersity index

Differential Scanning Calorimetry (DSC) of the PA of Examples 17a-17c

The glass transition temperatures of the MXD6 and of the PA of Examples 17a-17c were measured according to ASTM E1356 using a TA Instruments Model Q20/Q1000 Differential Scanning calorimeter fitted with refrigerating cooling system (RCS) operated with TA Thermal Advantage and Universal Analysis software. The instrument was calibrated using a heating and cooling rate of 10° C./min under nitrogen atmosphere at 50 ml/min. The measurements were also carried out using a heating and cooling rate of 10° C./min under nitrogen atmosphere.

With respect to MXD6, glass transition [83° C. ($T_g$) and melting temperature of 237° C. ($T_m$)] remained more or less unchanged, whereas a delay in crystallization of about 10-15° C. during the cooling cycle was observed, with an insignificant change in $\Delta H_c$.

Determination of the Glass Fiber Content

About 1 g of each composition prepared according to Example 18 was placed in a pre-weighed quartz fibre crucible. The quartz fibre crucible was then placed in a microwave furnace (Phoenix Airwave Microwave furnace from CEM). The temperature program was as follows: heating from room temperature to 500° C. in 2 hrs; maintenance at 500° C. for 2 minutes; 500° C. to 600° C. in 30 minutes; maintenance at 600° C. for 90 minutes; cooling from 600° C. to room temperature in 2 hrs. Once the furnace was cooled to room temperature, the crucible was removed and re-weighed using an analytical balance. The glass fiber content was calculated using the following formula:

Glass fiber (% wt) = [(wt of residue+wt of empty crucible)−wt of empty crucible]*100/[(wt of sample+wt of empty crucible)−wt of empty crucible]

The total glass fiber (GF) content is reported in Table 3.

TABLE 3

GF content in the compositions prepared according to Example 18

| Composition | Remarks | GF content (% wt) |
|---|---|---|
| Reference composition C-1* | MXD6 + glass fiber | 28.87 |

TABLE 3-continued

GF content in the compositions prepared according to Example 18

| Composition | Remarks | GF content (% wt) |
|---|---|---|
| C-1 | PA of Ex 17a + glass fiber | 28.18 |
| C-2 | PA of Ex 17b + glass fiber | 29.11 |
| C-3 | PA of Ex 17c + glass fiber | 29.09 |

Measurements of Contact Angles of Formed Articles

Static contact angles were measured against 2 μl each of water and n-hexadecane (HD) on 2 mm fibre-reinforced injection molded bars prepared as described in Example 19 using a Dataphysics Contact Angle System OCA 20 instrument according to the Sessile drop method. Images were captured after a fixed time of 10 seconds after dispensing the liquids (except in case of reference composition C-1* with HD, where it was immediate, as the drop used to spread too fast to be captured). Multiple data points (16-20) were collected and the average and standard deviation was calculated. The results are reported in Table 4 below.

TABLE 4

Static contact angles of molded bars prepared according to Example 19

| Contact Angle Against | Bar from ref. composition C-1* | Bar from ref. composition C-1 | Bar from ref. composition C-2 | Bar from ref. composition C-3 |
|---|---|---|---|---|
| Water (dry as molded) | 71.2 ± 0.5 | 79.5 ± 1.1 | 88.2 ± 2.2 | 92.4 ± 0.5 |
| Water (*annealed) | 79.5 ± 0.2 | 81.7 ± 1.1 | 92.2 ± 0.6 | 96.4 ± 1.6 |
| HD (dry as molded) | 12.1 ± 0.5 | 48.2 ± 1.9 | 73.7 ± 0.4 | 73.0 ± 0.3 |
| HD (*annealed) | 30.7 ± 1.8 | 50.5 ± 1.1 | 73.0 ± 0.2 | 74.7 ± 0.3 |

*annealed at 120° C. for 3 hours

Mechanical Tests on Formed Articles

Molded bars prepared according to Example 19 were tested as "dry as molded". For this purpose, after injection molding, the molded bars test bodies were stored for at least 48 h at room temperature in a desiccator in sealed aluminium bags. The tensile properties of the bars were measured according to the ISO 527 test procedure, while the notched and unnotched Izod impact strengths were measured according to the ISO 180 test procedure. Table 5 reports tensile strength, strain at break and modulus. Table 6 reports the impact strength data for unnotched and notched bars.

TABLE 5

Tensile strength of the molded bars prepared according to Example 19

| Molded bar | Modulus (GPa) | Tensile Strength (MPa) | Strain at Break (%) |
|---|---|---|---|
| Molded bar from ref composition C-1* | 11.6 ± 0.4 | 168 ± 5 | 1.17 ± 0.07 |
| Molded bar from composition C-1 | 11.3 ± 0.1 | 194 ± 4 | 1.47 ± 0.04 |

TABLE 5-continued

Tensile strength of the molded bars prepared according to Example 19

| Molded bar | Modulus (GPa) | Tensile Strength (MPa) | Strain at Break (%) |
|---|---|---|---|
| Molded bar from composition C-2 | 11.7 ± 0.1 | 203 ± 5 | 1.45 ± 0.05 |
| Molded bar from composition C-3 | 11.5 ± 0.6 | 204 ± 6 | 1.45 ± 0.10 |

TABLE 6

Impact strength of the molded bars prepared according to Example 19

| Molded bar | Unnotched IZOD impact strength (Kg/m2) | Notched IZOD impact strength (Kg/m2) |
|---|---|---|
| Molded bar from ref composition C-1* | 24.31 ± 0.70 | 7.38 ± 0.19 |
| Molded bar from composition C-1 | 31.04 ± 0.81 | 8.33 ± 0.18 |
| Molded bar from composition C-2 | 35.06 ± 1.37 | 9.04 ± 0.19 |
| Molded bar from composition C-3 | 35.44 ± 3.11 | 9.29 ± 0.26 |

The invention claimed is:

1. A polyamide (PA) consisting of recurring units derived from monomers (A) and (B), wherein monomer (A) is selected from at least one of:
   (i) a mixture of:
      one or more hydrogenated aliphatic, cycloaliphatic or aromatic diamine(s) [amine (NN)] or derivative(s) thereof; and
      one or more hydrogenated aliphatic, cycloaliphatic or aromatic dicarboxylic acid(s) [acid (DA)] or derivative(s) thereof; and
   (ii) one or more aminoacid(s) [aminoacid (AN)] or lactam(s) [lactam (L)], and wherein monomer (B) is at least one (per)fluoropolyether monomer (PFPE-M) selected from a PFPE-diamine (PFPE-NN) and PFPE-dicarboxylic acid (PFPE-DA), wherein the amount of monomer (B) ranges from 0.1 to 10% wt with respect to the overall weight of monomers (A) and (B).

2. The polyamide (PA) according to claim 1, wherein amine (NN) is an alkylene diamine having 2 to 36 carbon atoms.

3. The polyamide (PA) according to claim 1, wherein amine (NN) is an aromatic diamine selected from meta-xylylene diamine (MXDA), and para-xylylene diamine.

4. The polyamide (PA) according to claim 1, wherein acid (DA) is aromatic dicarboxylic acid comprising two reactive carboxylic acid groups [acid (AR)] or an aliphatic dicarboxylic acid comprising two reactive carboxylic acid groups [acid (AL)].

5. The polyamide (PA) according to claim 4, wherein acid (DA) is an acid (AL) selected from adipic acid and sebacic acid.

6. The polyamide (PA) according to claim 1, wherein (PFPE-DA) is a fluoropolymer comprising a fully or partially fluorinated polyalkyleneoxy chain [(per)fluoropolyoxylakylene chain $(R_f)$] having two chain ends, wherein each chain end comprises a —COOH group or a derivative thereof selected from salts, anhydrides, esters and acid halides and wherein (PFPE-NN) is a fluoropolymer comprising a fully or partially fluorinated polyalkyleneoxy chain [(per)fluoropolyoxylakylene chain $(R_f)$] having two chain ends, wherein each chain end comprises an amino group or a salt thereof.

7. The polyamide (PA) according to claim 6, wherein $(R_f)$ comprises recurring units R° having at least one catenary ether bond and at least one fluorocarbon moiety, and wherein said repeating units are randomly distributed along the chain and are selected from the group consisting of:
   (i) —CFXO—, wherein X is F or $CF_3$;
   (ii) —$CF_2$CFXO—, wherein X is F or $CF_3$;
   (iii) —$CF_2CF_2CF_2O$—; and
   (iv)—$CF_2CF_2CF_2CF_2O$—.

8. The polyamide (PA) according to claim 7, wherein chain $(R_f)$ comprises the following recurring units R°:
   (i) —$CF_2O$— and
   (ii)—$CF_2CF_2O$—
   wherein the molar ratio between recurring units (ii) and (i) ranges from 0.1 to 10.

9. The polyamide (PA) according to claim 6, wherein (PFPE-DA) and (PFPE-NN) comply with general formula (I):

$$A\text{-}O\text{-}R_f\text{-}A' \qquad (I)$$

wherein:
   $R_f$ is a fully or partially fluorinated polyalkyleneoxy chain;
   A and A' represent groups of formula:

$$CF_2\text{-}L_x\text{-}T$$

in which:
   L represents a bivalent radical selected from:
   (a) a $C_1$-$C_{20}$ straight or branched $C_3$-$C_{20}$ alkylene chain ($C_{alk}$), optionally containing one or more heteroatoms selected from O, N, S and P and/or one or more groups of formula —C(O)—, -C(O)O—, —OC(O)O—,—C(O)NH—,—NHC(O)NH—and —C(O)S—, said chain optionally containing a (heterocyclo)aliphatic ring ($R_{ali}$) or (heterocycloaromatic) ring ($R_{ar}$) as defined herein below;
   (b) a $C_3$-$C_{10}$ cycloaliphatic ring ($R_{ali}$), optionally substituted with one or more straight or branched alkyl groups, optionally containing one or more heteroatoms selected from N, O, S or groups of formula —C(O)—, —C(O)O—and —C(O)NH, and optionally further linked to or condensed with a further ring ($R_{ali}$) or with a $C_5$-$C_{12}$ aromatic or heteroaromatic ring ($R_{ar}$) as defined herein below, which can optionally be substituted with one or more straight or branched alkyl groups; or
   (c) a $C_5$-$C_{12}$ aromatic ring ($R_{ar}$), optionally containing one or more heteroatoms selected from N, O, S, optionally being substituted with one or more straight or branched alkyl groups and optionally further linked to or condensed with another equal or different ring ($R_{ar}$);
   x is 0 or 1;
   T is —COOH, —$NH_2$, or a derivative thereof.

10. The polyamide (PA) according to claim 9, wherein x is 1 and linking group L comprises one of the following groups directly bound to the —$CF_2$—group between chain ($R_f$) and linking group L: —$CH_2O$—, —$CH_2OC(O)NH$—, —$CH_2NR^1$—wherein $R^1$ is hydrogen or straight or branched $C_1$-$C_3$ alkyl, and —C(O)NH—.

11. A polyamide composition comprising at least one polyamide (PA) according to claim 1 in admixture with further ingredients and/or additives.

12. The polyamide composition of claim 11, wherein the at least one polyamide (PA) is in admixture with glass fibers.

13. A method for manufacturing the polyamide composition of claim 11, said method comprising mixing together the at least one polyamide (PA) with further ingredients and additives.

14. A formed article comprising at least one polyamide (PA) according to claim 1.

15. A formed article according to claim 14, said article being selected from a fuel line hose, a miniature circuit breaker, an electrical switch and a smart device.

16. A method for manufacturing a formed article comprising a polyamide (PA) according to claim 1, said method comprising:

melting the at least one polyamide (PA) according to claim 1 to obtain a molten polyamide (PA);
casting the molten polyamide (PA) into a mold; and
cooling.

17. A formed article comprising at least one polyamide composition of claim 11.

18. A formed article according to claim 17, said article being selected from a fuel line hose, a miniature circuit breaker, an electrical switch and a smart device.

19. A method for manufacturing a formed article comprising at least one polyamide composition of claim 11, said method comprising:

melting a polyamide composition according to claim 12 to obtain a molten polyamide composition;
casting the molten polyamide composition into a mold; and
cooling.

20. The polyamide (PA) according to claim 1, wherein the amount of monomer (B) ranges from 1 to 5% wt, with respect to the overall weight of monomers (A) and (B).

* * * * *